United States Patent
Thompson et al.

(10) Patent No.: US 7,557,914 B2
(45) Date of Patent: Jul. 7, 2009

(54) ROTATING LASER MEASUREMENT SYSTEM

(75) Inventors: Vincent Thompson, Seattle, WA (US); Stephen J. Bennison, Bellevue, WA (US); Scott L. Waltari, Auburn, WA (US)

(73) Assignee: The Boeing Company, Chicago, IL (US)

( * ) Notice: Subject to any disclaimer, the term of this patent is extended or adjusted under 35 U.S.C. 154(b) by 400 days.

(21) Appl. No.: 11/539,782

(22) Filed: Oct. 9, 2006

(65) Prior Publication Data

US 2008/0084558 A1    Apr. 10, 2008

(51) Int. Cl.
*G01N 21/00* (2006.01)

(52) U.S. Cl. .................. 356/241.1; 356/241.2; 356/614; 356/608

(58) Field of Classification Search ... 356/241.1–241.6, 356/614, 602, 623, 625, 607–608; 250/559.07, 250/559.22, 559.39, 559.49, 560
See application file for complete search history.

(56) References Cited

U.S. PATENT DOCUMENTS

| | | | | |
|---|---|---|---|---|
| 4,317,632 A | * | 3/1982 | Orphan et al. ........... | 356/241.1 |
| 4,355,904 A | * | 10/1982 | Balasubramanian ........ | 356/608 |
| 4,453,085 A | * | 6/1984 | Pryor ...................... | 250/203.1 |
| 4,967,092 A | * | 10/1990 | Fraignier et al. ........ | 250/559.07 |
| 5,099,115 A | * | 3/1992 | Cruickshank ............... | 250/236 |
| 5,177,779 A | * | 1/1993 | Cornu et al. ................ | 378/206 |
| 5,317,387 A | * | 5/1994 | Van Hengel et al. ........ | 356/625 |
| 5,416,574 A | * | 5/1995 | Fantone ...................... | 356/124 |
| 5,811,825 A | * | 9/1998 | Pryor et al. ............ | 250/559.21 |
| 5,933,231 A | * | 8/1999 | Bieman et al. ........... | 356/241.1 |
| 6,862,814 B2 | | 3/2005 | Bennison et al. | |
| 7,164,476 B2 | * | 1/2007 | Shima et al. ............. | 356/241.1 |

\* cited by examiner

*Primary Examiner*—Sang Nguyen
(74) *Attorney, Agent, or Firm*—Yee & Associates, P.C.; Dennis R. Plank (57) ABSTRACT

An apparatus including a scanning mechanism, a tracking mechanism, and a processing unit. The scanning mechanism includes a rotating mechanism, a mounting arm rotatably attached to the rotating mechanism, and a light source connected to the mounting arm. The scanning mechanism also includes a mirror connected to the mounting arm, wherein the mirror is positioned to reflect the coherent light. The scanning mechanism also includes a measuring system attached to the mounting arm. The measuring system measures a parameter associated with an object on which the coherent light falls. The tracking mechanism is in communication with the scanning mechanism. The tracking mechanism measures a distance from the tracking mechanism to the scanning mechanism. The processing unit is in communication with the scanning mechanism and the tracking mechanism. The processing unit collects measurement information from the scanning mechanism and the tracking mechanism.

21 Claims, 8 Drawing Sheets

ROTATING LASER MEASUREMENT SYSTEM

BACKGROUND OF THE INVENTION

1. Field of the Invention

The present invention relates generally to measuring objects and more particularly to improved systems for measuring internal parameters of a cavity.

2. Description of the Related Art

In many different fields, and particularly in aerospace engineering, various parameters for items are measured to ensure that the items, when manufactured, meet design specifications. These design specifications are specified as parameters needed for the item to perform properly. Design specifications may include, for example, dimensions, weight, and composition. The parameters may have tolerances within which the different parameters should fall.

For example, with a newly manufactured wing, a number of parameters for the wing should be within specified tolerances. In other words, the parameters should not vary beyond whatever range that is specified for a particular tolerance. These parameters include dimensions for different parts of the wing, such as the height, straightness, angle, and spacing of cavities and internal surface of cavities within the wing. These parameters are measured to ensure that the wing will perform properly and safely once the wing is mounted to an airplane. If, for example, the newly manufactured wing does not meet desired tolerances, then the wing is modified to ensure compliance with the desired tolerances or the wing will be discarded in favor of a new wing that does meet desired tolerances.

Some items are designed to have internal cavities. For some of these items, the parameters of the internal cavities are measured to ensure that these parameters meet desired tolerances. For example, many types of aircraft wings have internal cavities that have specified dimensions.

Measuring an internal cavity within an object, such as a wing, may be challenging. Currently, in some cases, the different pieces of the wing may be measured before these pieces are put together. In other cases, the wing is formed in one piece with the cavities. In this case, the parameters of the internal cavities can be measured only by taking apart the wing. However, this solution is undesirable because taking apart the wing makes the wing unusable.

Thus, currently, a prototype aircraft wing is constructed, opened, and then measured. If the tolerances for the prototype wing are met, then production wings are made to fill orders. Purchasers have to trust that these subsequently manufactured aircraft wings have the same desired tolerances.

However, trusting that an aircraft wing meets desired tolerances usually is unacceptable because of the strong desire to produce safe aircraft. Furthermore, aircraft wings are expensive and time-consuming to manufacture. Therefore, it would be advantageous to have an improved method and apparatus to measure the internal parameters of a cavity within an object.

SUMMARY OF THE INVENTION

An embodiment of the present invention provides a method and apparatus for measuring a parameter in a cavity. An apparatus includes a scanning mechanism, a processing unit, and a tracking mechanism. The scanning mechanism includes a rotating mechanism, a mounting arm rotatably attached to the rotating mechanism, and a light source connected to the mounting arm. The light source emits a coherent light. The scanning mechanism also includes a mirror connected to the mounting arm, wherein the mirror is positioned to reflect the coherent light. The scanning mechanism also includes a measuring system attached to the mounting arm. The measuring system measures a parameter associated with an object on which the coherent light falls. The tracking mechanism is in communication with the scanning mechanism. The tracking mechanism measures a distance from the tracking mechanism to the scanning mechanism. The processing unit is in communication with the scanning mechanism and the tracking mechanism. The processing unit collects measurement information from the scanning mechanism and the tracking mechanism.

The features, functions, and advantages may be achieved independently in various embodiments of the present invention or may be combined in yet other embodiments. Thus, the illustrative embodiments described herein may take a variety of forms.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an advantageous embodiment of the present invention when read in conjunction with the accompanying drawings, wherein:

DETAILED DESCRIPTION OF THE PREFERRED EMBODIMENT

Figure 1:
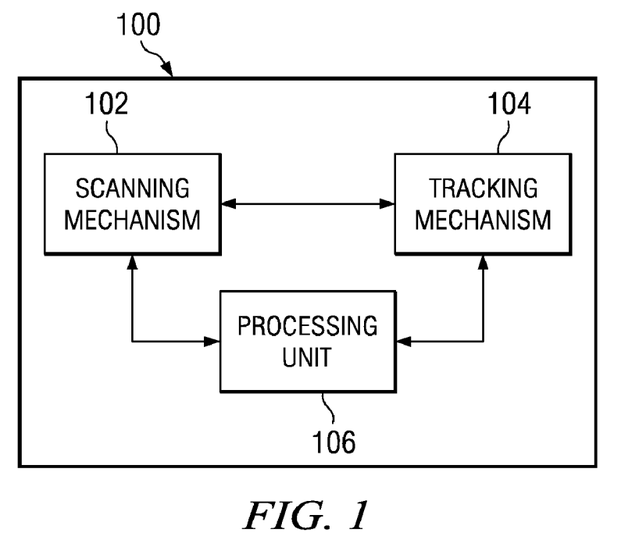
FIG. 1 is a block diagram of a scanning system in accordance with an advantageous embodiment of the present invention.

With reference now to the figures and in particular with reference to FIG. 1, a block diagram of a scanning system is depicted in accordance with an advantageous embodiment of the present invention. Scanning system 100 may be used to measure parameters of an object. In particular, scanning system 100 may be used to measure internal parameters inside the object. A parameter is a physical characteristic of an object that can be measured. A parameter includes, for example, dimensions, mass, density, consistency, reflectivity, opacity, color, or any other physical property of an object. From these parameters other derived parameters of an object can be determined, such as size, shape, or other characteristics. An internal parameter, in these advantageous embodiments, refers to a parameter of a cavity within an object, any surfaces of the cavity, and any materials that form the cavity. In one illustrative embodiment, scanning system 100 may be used to measure a set of internal parameters for an aircraft part, such as a horizontal stabilizer, without damaging the horizontal stabilizer. The set of internal parameters is one or more parameters in these examples. In particular, scanning system 100 may be used to measure a set of internal parameters, such as the dimensions of a cavity in a horizontal stabilizer.

In this illustrative example, scanning system 100 includes scanning mechanism 102, tracking mechanism 104, and processing unit 106. Together, scanning mechanism 102, tracking mechanism 104, and processing unit 106 may be used to measure a set of internal parameters for a number of cavities within an object. Further, a three dimensional model of a group of internal cavities may be generated using the data measured by scanning system 100. In conjunction with measurements of parameters on the outside of an object, scanning system 100 may provide data to create a three dimensional model of an entire object. In one illustrative example, scanning system 100 may be used to model a group of cavities of a horizontal stabilizer without damaging the stabilizer. In conjunction with measurements of parameters on the outside of the horizontal stabilizer, scanning system 100 can provide a three dimensional model of this object.

In these illustrative examples, scanning mechanism 102 is inserted into a cavity to be measured or modeled. With scanning system 100, the cavity may be accessed without damaging the object. Tracking mechanism 104 tracks the position of scanning mechanism 102 within the cavity relative to the overall object or some other reference. Scanning mechanism 102 is then used to acquire data regarding a set of internal parameters for the cavity. Processing unit 106 uses internal parameters measured by tracking mechanism 104 and scanning mechanism 102 to calculate derived parameters, such as size and shape, if desired. Thus, processing unit 106 can use measured internal parameters to form a model of the cavity.

Figure 2:
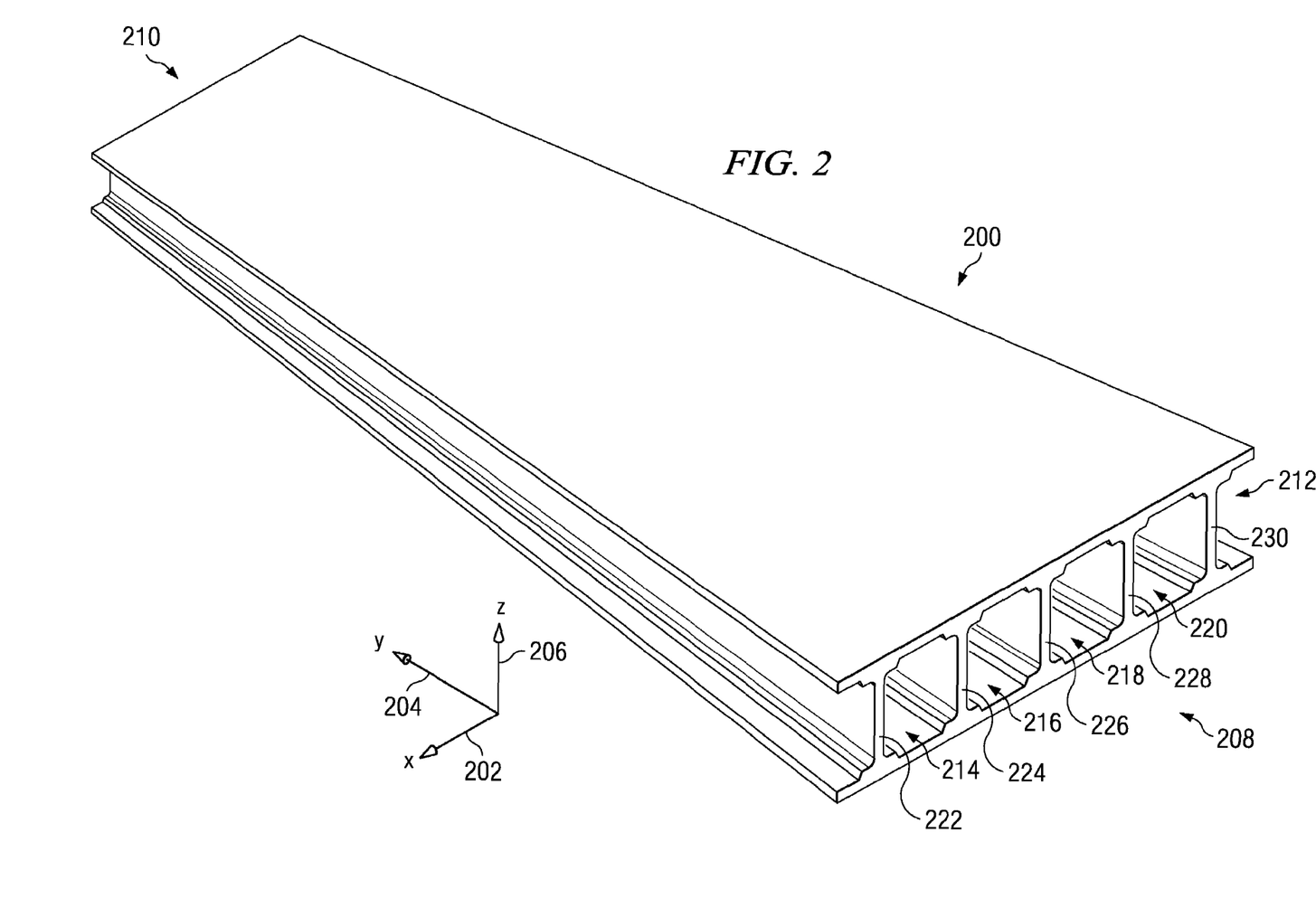
FIG. 2 is a diagram of perspective view a horizontal stabilizer, which may be measured in accordance with an advantageous embodiment of the present invention.

Next, FIG. 2 is a diagram of perspective view a horizontal stabilizer, which may be measured in accordance with an advantageous embodiment of the present invention. Horizontal stabilizer 200 is an example of an object having a set of cavities in which a scanning system, such as scanning system 100 of FIG. 1, may be used to measure a set of internal parameters within the set of cavities. Horizontal stabilizer 200 is illustrated together with X-axis 202, Y-axis 204, and Z-axis 206 for reference. However, the illustrative embodiments are not limited to any particular coordinate system, so the coordinate system disclosed herein may be varied without affecting the scope of the illustrative embodiments.

In this example, horizontal stabilizer 200 is a type of wing for an aircraft. Specifically, horizontal stabilizer 200 is the relatively short wing mounted to the tail of an aircraft. Although the illustrative embodiments presented herein are described with respect to horizontal stabilizer 200, the scanning mechanism may be used in any type of wing having cavities and, most generally, the scanning mechanism may be used in any object having cavities. The measurements made by a scanning mechanism are made without destroying or damaging the object.

Measuring a set of internal parameters of cavities of horizontal stabilizer 200 may be challenging due to the length and varying dimensions of horizontal stabilizer 200. In this illustrative example, horizontal stabilizer 200 is eight feet wide along X-axis 202 at end 208, two feet wide along X-axis 202 at second end 210, and forty feet long along Y-axis 204 along end 212. Horizontal stabilizer 200 is approximately two feet in height along Z-axis 206 at end 208 and six inches in height along Z-axis 206 at second end 210. Different horizontal stabilizers can have different dimensions.

In this particular illustrative example, horizontal stabilizer 200 has a set of four cavities, cavity 214, cavity 216, cavity 218, and cavity 220. Cavities 214, 216, 218, and 220 may have different shapes due to the presence of structures that define those cavities. For example, I-shaped structure 222, I-shaped structure 224, I-shaped structure 226, I-shaped structure 228, and I-shaped structure 230 define shapes for cavities 214, 216, 218, and 220 as illustrated in FIG. 2.

Figure 3:
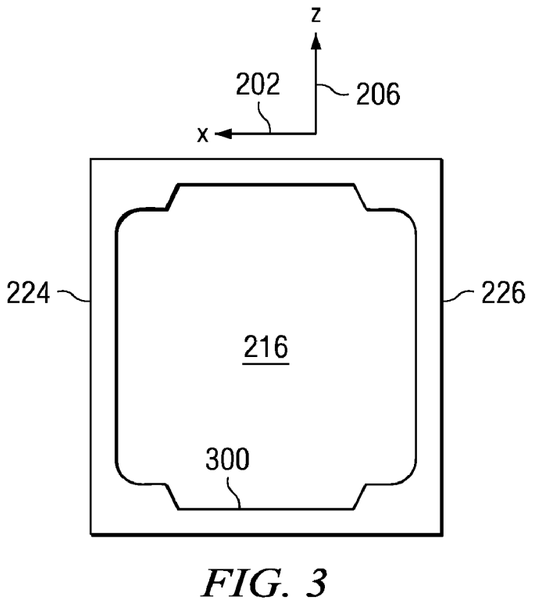
FIG. 3 is a diagram illustrating a cross section of a portion of a horizontal stabilizer in FIG. 2, which may be measured in accordance with an advantageous embodiment of the present invention.

FIG. 3 is a diagram illustrating a cross section of a portion of a horizontal stabilizer in FIG. 2, which may be measured in accordance with an advantageous embodiment of the present invention. Specifically, FIG. 3 is a cross section view of cavity 216 in horizontal stabilizer 200 in FIG. 2. Therefore, reference numerals in FIG. 3 refer to corresponding parts or structures shown in FIG. 2.

In particular, FIG. 3 illustrates a slice of cavity 216 located at end 208 of horizontal stabilizer 200 relative to X-axis 202. In one illustrative embodiment cavity 216 is approximately two feet about X-axis 202 and approximately two feet about Z-axis 206. Inside surface 300 of cavity 216 has a shape that varies due to the presence of I-shaped structure 224 and I-shaped structure 226. In particular, cavity 216 is slightly larger along Z-axis 206 in the central portion of the cavity relative to X-axis 202.

Figure 4:
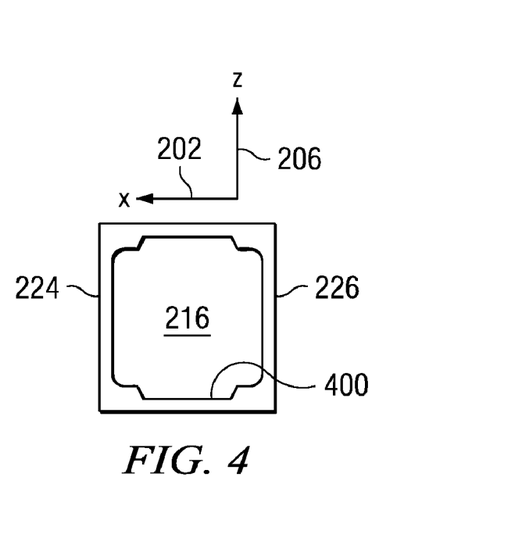
FIG. 4 is a diagram illustrating a cross section of a portion of a horizontal stabilizer in FIG. 2, which may be measured in accordance with an advantageous embodiment of the present invention.

FIG. 4 is a diagram illustrating a cross section of a portion of a horizontal stabilizer in FIG. 2, which may be measured in accordance with an advantageous embodiment of the present invention. Specifically, FIG. 4 is a cross section view of cavity 216 in horizontal stabilizer 200 in FIG. 2. Therefore, reference numerals in FIG. 4 refer to corresponding parts or structures shown in FIG. 2.

In particular, FIG. 4 illustrates a slice of cavity 216 located at end 210 of horizontal stabilizer 200 relative to X-axis 202. In one illustrative embodiment cavity 216 is approximately six inches about X-axis 202 and approximately six inches about Z-axis 206. Inside surface 400 of cavity 216 has a shape that varies due to the presence of I-shaped structure 222 and I-shaped structure 224. In particular, cavity 216 is slightly larger along Z-axis 206 in the central portion of the cavity relative to X-axis 202.

Together, FIGS. 2 through 4 illustrate that cavity 216 of horizontal stabilizer 200 is long and is approximately two feet across at end 208 and only six inches across at end 210. Because the dimensions of the cavity change along the length of the horizontal stabilizer, measuring the internal dimensions is both highly desirable and challenging.

Horizontal stabilizer 200 is, in this illustrative example, manufactured as a single graphite composite structure. Verification that internal parameters of cavities 214, 216, 218, and 220 meet specifications for this part is desirable. Scanning system 100 of FIG. 1 may be used to measure the set of internal parameters of horizontal stabilizer 200 without taking this component apart to make the measurements as is required with currently used techniques. As a result, damage to horizontal stabilizer 200 is avoided using scanning system 100 to measure the set of internal parameters of cavities 214, 216, 218, and 220. The scanning mechanism in scanning system 100 used to measure these cavities is described in FIG. 1 is described in more detail below in FIG. 5.

Figure 5:
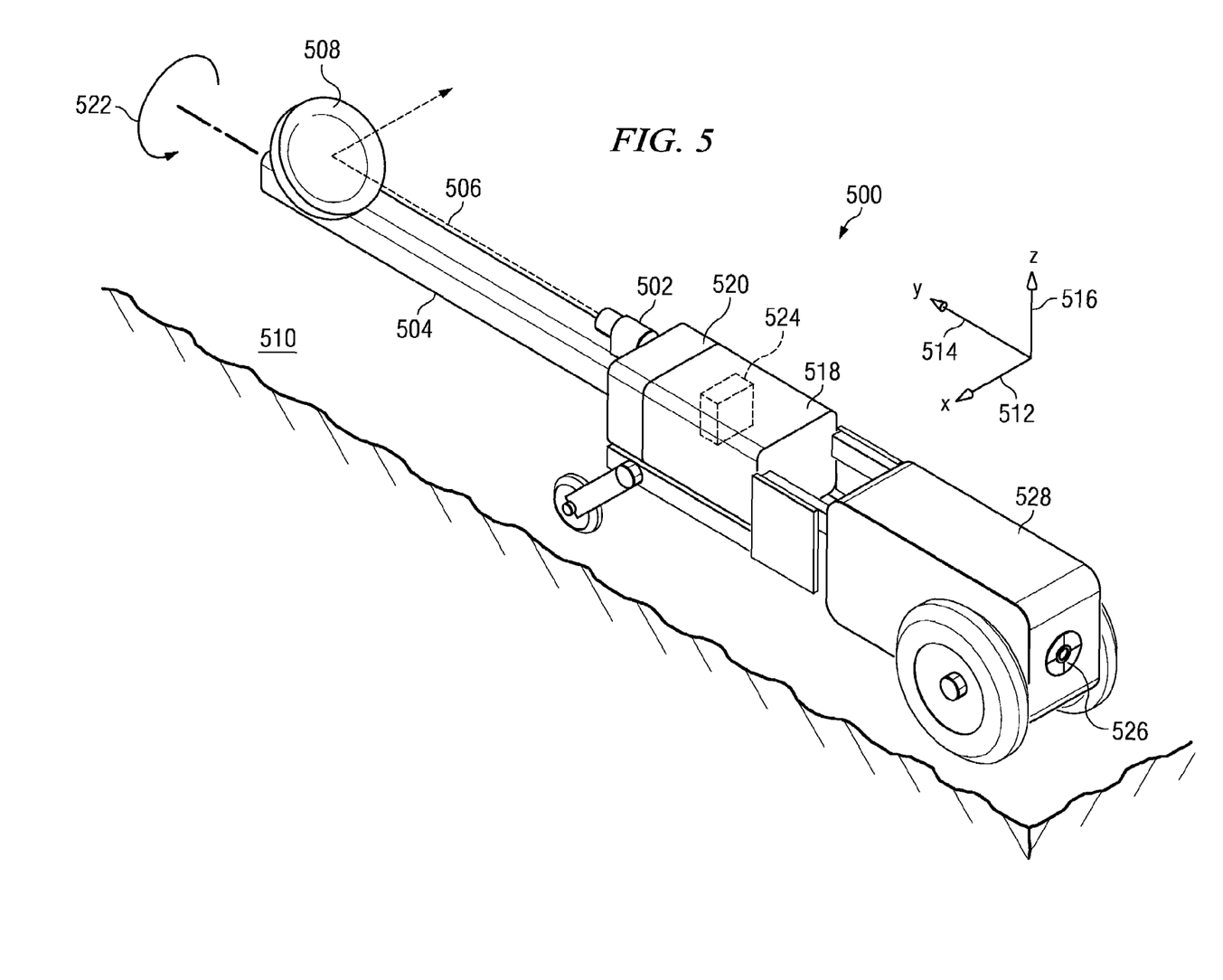
FIG. 5 is a diagram of a perspective view of a scanning mechanism in accordance with an advantageous embodiment of the present invention.

With reference now to FIG. 5, a diagram of a perspective view of a scanning mechanism is depicted in accordance with an advantageous embodiment of the present invention. Scanning mechanism 500 may be used to implement scanning mechanism 102 of FIG. 1. Thus, scanning mechanism 500 may be used to measure various internal parameters of a cavity within an object, such as horizontal stabilizer 200 depicted in FIG. 2.

In this example, scanning mechanism 500 uses light to measure a set of internal parameters of the cavity. As depicted, light source 502 generates the light and is attached to mounting arm 504. In the illustrative embodiment described in FIG. 5, light source 502 is positioned on mounting arm 504 such that optical path 506 strikes mirror 508. Mirror 508 deflects optical path 506 away from mirror 508 and mounting arm 504. The light from light source 502 follows optical path 506 such that the light falls on a point on inside surface 510 of the cavity.

In this illustrative embodiment, light source 502 is a measuring system capable of measuring a distance between light source 502 and a point on inside surface 510 of the cavity. In other illustrative embodiments, light source 502 may be provided in addition to a measuring system. In other embodiments, light source 502 and the measuring system may be located in the same housing. An example of such a combined light source and measuring system is the LT-9000 Series Laser Confocal Displacement Meter available from Keyence Corporation headquartered in Osaka, Japan, which can be used in place of light source 502 of FIG. 5. Specifically, the output of the laser yields a voltage output which may be calibrated to distance or range. Other examples of measuring systems include light detection and ranging (LIDAR) systems, sound detection and ranging (SONAR) systems, conoscopic holography systems, focusing method system, and other measurement systems.

Scanning mechanism 500 is illustrated together with X-axis 512, Y-axis 514, and Z-axis 516 for reference. However, the illustrative embodiments are not limited to any particular coordinate system, so the coordinate system disclosed herein may be varied without affecting the scope of the illustrative embodiments. X-axis 512, Y-axis 514, and Z-axis 516 are illustrated relative to the scanning mechanism in relation to a cavity into which the scanning mechanism is inserted. Thus, for example, Y-axis 514 points along the long axis of mounting arm 504 and also along the direction into which scanning mechanism 500 is inserted into a cavity.

In the illustrative embodiment of FIG. 5, mounting arm 504 is rotatably attached to rotating mechanism 518 via optional gear reduction assembly 520. The term rotatably attached means that two components are attached to each other, perhaps via one or more other components, such that one or both of the two components can rotate. An example of a rotatably attached component is mounting arm 504, which is attached to rotating mechanism 518 such that when rotating mechanism 518 rotates, mounting arm 504 also rotates. Mounting arm 504 may be attached to rotating mechanism 518 in a number of ways.

For example, mounting arm 504 may be mounted directly to rotating mechanism 518 or may be mounted to rotating mechanism 518 using other parts between these two components. In this depicted example, mounting arm 504 can rotate about Y-axis 514 as rotating mechanism 518 rotates. Optional gear reduction assembly 520 can aid rotating mechanism 518 in rotating mounting arm 504 at a desired angular velocity.

In addition, angular encoder 524 is attached to rotating mechanism 518. Angular encoder 524 measures an angle through which mounting arm 504 rotates. In one illustrative embodiment, angular encoder 524 can measure changes of 5000 steps in one full revolution of mounting arm 504. Angular encoder 524 may be attached to any part of scanning mechanism 500, such that angular encoder 524 is able to measure an angle through which mounting arm 504 rotates.

Additionally, retroreflector 526 may be attached to a convenient portion of scanning mechanism 500. In the illustrative embodiment illustrated in FIG. 5, retroreflector 526 is attached to the proximal end of rotating mechanism 518. Retroreflector 526 reflects light from a tracking mechanism, such as tracking mechanism 104 of FIG. 1. The tracking mechanism may determine the total distance of the optical path followed by light traveling from the scanning mechanism to the retroreflector and back to the scanning mechanism. In this manner, the tracking mechanism measures a distance from the tracking mechanism to retroreflector 526. Because retroreflector 526 is attached to scanning mechanism 500, the distance from the tracking mechanism to scanning mechanism 500 is also known. This distance may be used to track the position of scanning mechanism 500 within the cavity with respect to the object being measured.

Optionally, robot 528 may be attached to scanning mechanism 500, and in particular to rotating mechanism 518. Robot 528 may be, for example, a remote controlled vehicle that moves scanning mechanism 500 within the cavity being measured. Robot 528 also may be the end of a mechanical boom operated externally from scanning mechanism 500. In any case, robot 528 is dimensioned such that mounting arm 504, light source 502, and mirror 508 can rotate within the cavity. Thus, for example, the height of robot 528 along Z-axis 516 may be created or adjusted to allow mounting arm 504, light source 502, and mirror 508 to rotate without touching or scraping inside surface 510 or other inside surfaces of the cavity being measured.

In use, scanning mechanism 500 is inserted into the cavity to be measured. A first measurement of an internal parameter of the cavity is taken. In this illustrative embodiment, the first measurement is the distance along optical path 506 from light source 502 to a point on the inside surface of the cavity.

Rotating mechanism 518 then rotates mounting arm 504 through a measured angle about Y-axis 514 as illustrated by arrows 522. Accordingly, light source 502 and mirror 508 are rotated through the same angle along with mounting arm 504. A second measurement of distance is taken at the new angular position of mounting arm 504.

The first and second distances, possibly together with other measured distances, may be used to measure the dimensions of the cavity in a plane parallel to a plane containing Z-axis 516 and X-axis 512. A set of measurements of the internal parameters of the cavity in such a plane may be used to produce a three dimensional slice of the cavity. Multiple slices may be used to produce a model of the overall cavity within the object being measured.

Thereafter, robot 528 translates or moves scanning mechanism 500 a translational distance along Y-axis 514. The translational distance moved may be measured by a tracking mechanism, such as tracking mechanism 104 of FIG. 1. The process of measuring a distance along optical path 506 is repeated for several different angular positions of mounting arm 504. The process of moving scanning mechanism 500 a measured translational distance and measuring the distance along optical path 506 at one or more angular positions of mounting arm 504 is repeated a desired number of times. Together, the set of measurements of optical paths and translational distances may be used to model the dimensions of the cavity within the object.

The individual components of scanning mechanism 500 are available from a variety of vendors or may be manufactured without undue effort. For example, mounting arm 504 may be a solid aluminum housing or rod, or some other relatively rigid material suitable for mounting light source 502 and mirror 508.

Although light source 502 is implemented using a LT-9000 Series Laser, other types of measuring systems may be used to measure the distance along optical path 506. For example, in other embodiments, mirror 508 is unnecessary when light source 502 can directly shine light on an inside surface of the cavity to be measured and a measurement of the distance of the optical path taken. In another illustrative embodiment, light source 502 may be some other triangulation based measuring system that uses a laser or other coherent light to project a spot on the surface to be measured while an optical array on the measuring system senses the location of the spot. Additionally, light source 502 may be a source other than a laser light source. For example, light source 502 may be a light emitting diode (LED) or some other light source.

Mirror 508 may be implemented using any mirror suitable for reflecting light from light source 502. In one illustrative embodiment, mirror 508 is a mirror having a reflectivity of sufficient quality to allow a coherent light to be reflected from the surface of the mirror without scattering or diffracting the coherent light by an undesirable amount. Mirror 508 is illustrated as having a cylindrical shape; however, the shape of mirror 508 may be varied without affecting the operation of scanning mechanism 500. The distance along Y-axis 514 from light source 502 to mirror 508 can also be varied, depending on the exact type of light source or measuring system used.

Gear reduction assembly 520 is, in these examples, an assembly of mechanical components suitable for creating gear reduction. This component is used because some types of motors have a minimum rotation speed that, if not adjusted, will rotate mounting arm 504 faster than desired. Gear reduction assembly 520 translates a rotation of rotating mechanism 518 through a first angle to a rotation of mounting arm 504 through a second angle. The second angle is usually less, sometimes much less, than the first angle.

Thus, while rotating mechanism 518 might rotate through a large angle, gear reduction assembly 520 allows rotating arm 504 to rotate through only a small angle. Different types of gear reduction assemblies may be used as desired with scanning mechanism 500. In some cases, gear reduction assembly 520 is not needed if the angular velocity of rotating mechanism 518 is not too fast.

Angular encoder 524 may be implemented using any device suitable for measuring an angle through which mounting arm 504 rotates. In this example, angular encoder 524 may be implemented using an angular encoder available from Heidenhain Corporation of Schaumburg, Ill.

Rotating mechanism 518 may be, for example, a rotational stepping motor or any device suitable for creating torque. A rotational stepping motor is a brushless, synchronous electric motor that can divide a full rotation into a large number of steps, for example, 500 steps. A rotational stepping motor may have more or fewer steps. Rotational stepping motors are available from a variety of vendors, such as Teknic of Pittsford, located in New York. Additionally, other types of motors or devices for producing torque may be used to implement rotating mechanism 518. The rotating mechanism does not need to be a powered device. Instead, the mechanism may be one that allows a person to manually rotate mounting arm 504.

Retroreflector 526 may be any suitable retroreflector, mirror, or other device to allow the tracking mechanism to track the position of the scanning mechanism relative to the tracking mechanism. Retroreflectors reflect light back in the direction from which the light arrived. Retroreflectors are available from a variety of vendors, such as PLX, Inc. located in Deer Park, N.Y. In other illustrative embodiments, retroreflector 526 may be replaced with some other mechanism for measuring a distance between the tracking system and scanning mechanism 500, such as a radar ranging device or some other device.

Robot 528 may be a variety of devices suitable for moving scanning mechanism 500. For example, robot 528 may be a two-wheeled vehicle that pushes, pulls, or turns scanning mechanism 500. Robot 528 may be a vehicle with treads or some other number of wheels. Robot 528 may be replaced by a boom that moves scanning mechanism 500 in and out of the cavity to be measured.

Figure 6:
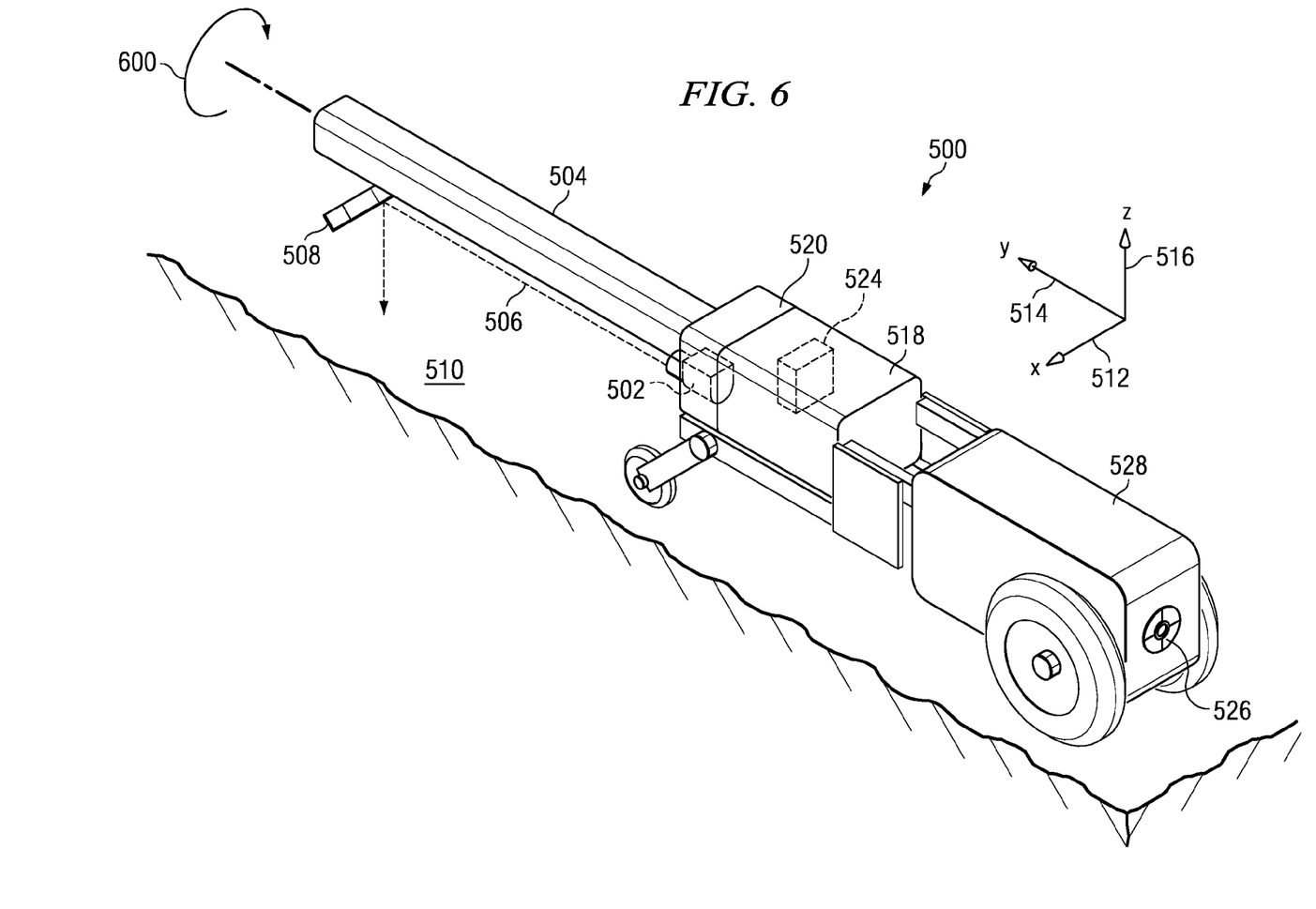
FIG. 6 is a diagram of a perspective view of a scanning mechanism in accordance with an advantageous embodiment of the present invention.

Next, FIG. 6 is a diagram of a scanning mechanism in accordance with an advantageous embodiment of the present invention. The various parts illustrated and described in FIG. 6 correspond to similar parts illustrated and described in FIG. 5. Thus, reference numerals used in FIG. 5 are repeated in FIG. 6 to refer to the same part or component. In FIG. 6, mounting arm 504 of scanning mechanism 500 has rotated 180 degrees about Y-axis 514 in the direction of arrow 600.

Figure 7:
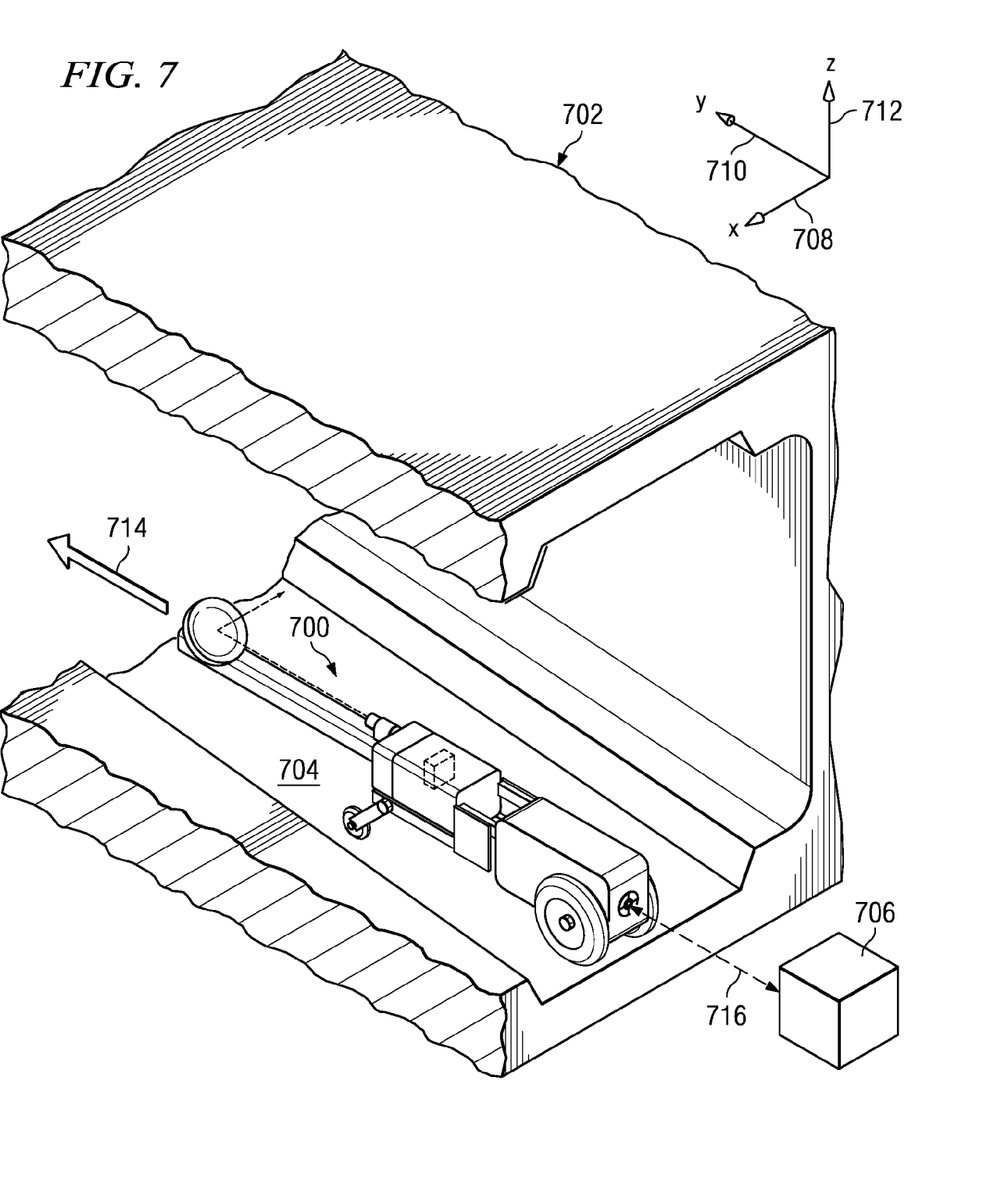
FIG. 7 is a diagram of a perspective view of a scanning mechanism in use on a cavity of a horizontal stabilizer in accordance with an advantageous embodiment of the present invention.

With reference now to FIG. 7, a diagram of a perspective view of a scanning mechanism in a cavity of a horizontal stabilizer is depicted in accordance with an advantageous embodiment of the present invention. In this example, scanning mechanism 700 is a scanning mechanism, such as scanning mechanism 102 of FIG. 1 and scanning mechanism 500 of FIG. 5. Horizontal stabilizer 702 corresponds to horizontal stabilizer 200 of FIG. 2 and cavity 704 corresponds to cavity 216 of FIGS. 2 through 4. Tracking mechanism 706 corresponds to tracking mechanism 104 of FIG. 1. X-axis 708 corresponds to X-axis 202 of FIG. 2, Y-axis 710 corresponds to Y-axis 204 of FIG. 2, and Z-axis 712 corresponds to Z-axis 206 of FIG. 2.

Scanning mechanism 700 is inserted into cavity 704, as illustrated by arrow 714. A first measurement of an internal parameter of the cavity is taken. In an illustrative embodiment, the internal parameter is a distance measurement from the scanning mechanism to an internal surface of cavity 704. The mounting arm of scanning mechanism 700 is rotated through a measured angle about Y-axis 710. In response, the light source and the mirror attached to the mounting arm are rotated through the same angle. A second distance measurement is taken at the new angular position of the mounting arm. The first and second distance measurements, possibly together with other measured distances, may be used to measure the dimensions of the cavity in a plane parallel to a plane containing Z-axis 712 and X-axis 708. The set of one or more measurements of the internal parameters of the cavity in such a plane can thereby produce a three dimensional slice of the cavity. Multiple slices along different points along Y-axis 710 may be used to produce a model of the overall cavity within the object being measured.

After taking a slice of the internal dimensions of cavity 704, the robot translates or moves the scanning mechanism a translational distance along Y-axis 710. The translational distance moved may be measured by tracking mechanism 706. In an illustrative example, the translational distance moved along Y-axis 710 may be measured by shining a light, such as laser light 716, onto a retroreflector attached to scanning device 700. Known techniques are then used to measure the distance from tracking mechanism 706 to scanning mechanism 700.

In the illustrative examples, the process of measuring a parameter of the cavity is repeated for several different angular positions of the mounting arm of scanning mechanism 700. The process of moving scanning mechanism 700 a measured translational distance and then again measuring the parameter at one or more angular positions of the mounting arm is repeated a desired number of times. Together, the set of measurements of optical paths and translational distances may be used to model the dimensions of cavity 704 in horizontal stabilizer 702.

Figures 8, 9, 10:
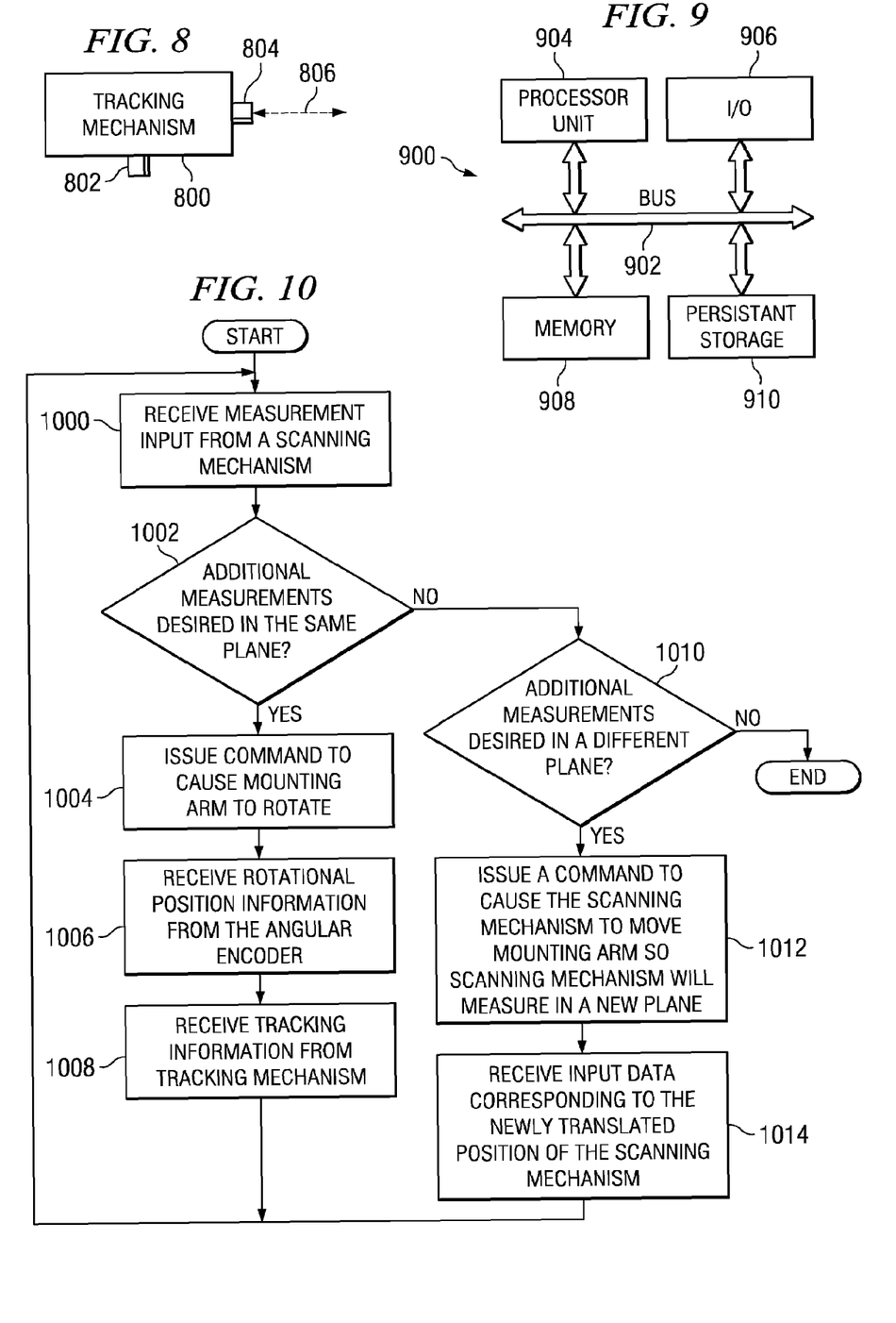
FIG. 8 is a block diagram of a tracking mechanism in accordance with an advantageous embodiment of the present invention.
FIG. 9 is a block diagram of a processing unit in accordance with an advantageous embodiment of the present invention.
FIG. 10 is a flowchart of a process for measuring internal cavities in accordance with an advantageous embodiment of the present invention.

With reference to FIG. 8, a block diagram of a tracking mechanism is depicted in accordance with an advantageous embodiment of the present invention. Tracking mechanism 800 is an example of a tracking mechanism that may be used to implement tracking mechanism 104 of FIG. 1. Although the illustrative embodiment of a tracking mechanism described in FIG. 8 is an interferometer, other types of tracking mechanisms may be used, to implement to tracking mechanism 104 of FIG. 1.

Tracking mechanism 800 may be implemented using any device suitable for measuring a distance between tracking mechanism 800 and a scanning mechanism, such as scanning mechanism 102 of FIG. 1 and scanning mechanism 500 of FIG. 5. An example of a tracking mechanism is an interferometer, which is a device that measures small changes in interference patterns of light waves as a result of a change in distance between objects. A small change in distance may be correlated to a change in interference patterns of the light waves. As a result, changes in distance on the order of the wavelength of the light being used may be measured using an interferometer. Many different types of interferometers exist and may be used in tracking mechanism 800.

An interferometer may be used to measure the position of a scanning mechanism relative to the interferometer. This information may be used to setup a reference system to which measurements of a set of internal parameters of a cavity within an object may be correlated. In this way, tracking mechanism 800 together with a scanning mechanism enable a processor and appropriate software to produce a model of the dimensions of an object.

Modeling software is known. Examples of modeling software include CAD programs and modeling software available from companies such as SolidWorks Corporation located in Concord, Mass. and mathematical and statistical programs such as MLAB available from Civilized Software Inc. located in Silver Spring, Md.

In the illustrative example provided in FIG. 8, interferometer 800 includes communication port 802 and light port 804. Laser light 806 exits and enters light port 804 according to the type of interferometer used. Communication port 802 allows interferometer 800 to communicate with a processor, such as processing unit 106 of FIG. 1.

Next, FIG. 9 is a block diagram of a processing unit in accordance with an advantageous embodiment of the present invention. Processing unit 900 may be used to implement processing unit 106 of FIG. 1. Processing unit 900 may be any suitable data processing system, such as a personal computer, personal digital assistant, a mobile computer, or any suitable processor or data processing system for operating computer-usable code in a recordable-type medium.

Processing unit 900 includes bus 902 which allows various other components of processing unit 900 to communicate with each other. In particular, bus 902 is in communication with processor 904, which executes computer usable program code for producing a slice or a model of an object. An example of a processor is an Intel Pentium IV® processor, though many different processors may be used.

Bus 902 is also in communication with input/output device 906. Input/output device 906 allows processing unit 900 to communicate with various external devices, such as tracking mechanism 104 of FIG. 1 and scanning mechanism 102 of FIG. 1. An example of an input/output device is an Ethernet port, though many different input/output devices may be used.

Bus 902 is also in communication with memory 908. Memory 908 includes computer usable program code for producing a slice or a model of an object. The computer usable program code correlates the translational position of the scanning mechanism within the object relative to the tracking mechanism, the angular position of the mounting arm of the scanning mechanism, and the measurement of the desired internal parameter at that particular translational position and angular position. The measurement of the internal parameter at that point is then correlated with other, additional, measurements of internal parameters at other translational positions and angular positions in order to form a three dimensional model of the cavity within the object.

The model of one cavity within an object may be correlated to other models of other cavities within the object in order to produce a three dimensional model of the set of cavities within the object. Together with measurements of parameters on the outside of the object, a total wire-frame model of the object may be produced that describes both the internal parameters of the object and the external parameters of the object.

In FIG. 9, bus 902 is also in communication with persistent storage 910. Persistent storage 910 can also contain computer usable program code as described above. Persistent storage 910 can also contain data collected by performing measurements with the tracking mechanism and the scanning mechanism.

FIG. 10 is a flowchart of process for measuring internal cavities in accordance with an advantageous embodiment of the present invention. The process described in FIG. 10 may be implemented in computer usable program code executed by processing unit 900 of FIG. 9 for use in a scanning system, such as scanning system 100 described in FIG. 1. In an exemplary illustrative embodiment, the process described in FIG. 10 is implemented using a scanning mechanism to measure a set of internal parameters of a cavity of a horizontal stabilizer, as described with respect to FIG. 2. The exemplary process described in FIG. 10 takes place after the scanning system has been setup and calibrated and after the scanning mechanism has been inserted into a cavity at an initial position.

The process begins by receiving measurement input from a scanning mechanism (operation 1000). The measurement input corresponds to a measurement taken by the scanning mechanism of an internal parameter associated with a point on the inside surface of the cavity. The process then determines whether additional measurements are desired in the same plane as the last measured point (operation 1002). The same plane may be, for example, a plane parallel to X-axis 202 and Z-axis 206 of FIG. 2. If additional measurements within the same plane are desired, then the process issues a command that causes the mounting arm to rotate (operation 1004). However, in other embodiments, a user can cause the arm to rotate either by issuing the command, by manually rotating the mounting arm, or rotating the mounting arm in some other manner. Using an angular encoder, the scanning mechanism measures the rotational change of the mounting arm to determine a new rotational position of the mounting arm. In turn, the process receives rotational position information from the angular encoder (operation 1006). Thus, the measured rotational change produces a measurement of an angle through which the mounting arm rotated.

For some illustrative embodiments, a reference point, such as a second mirror, can be attached to the mounting arm in the same plane as the laser beam. A tracking mechanism, such as tracking mechanism 104 of FIG. 1 can be used track the position of the reference point as the mounting arm rotates. As the mounting arm rotates, the reference point inscribes a circle in the same plane being measured. The tracking mechanism can measure the location of the reference point and use this information to create a references system for the cavity while the scanning mechanism performs measurements. For these types of embodiments, the process shown in FIG. 10 further includes the operation of receiving tracking information from a tracking mechanism (operation 1008).

Whether or not operation 1008 is used, the process then returns to operation 1000. At that point, an internal parameter of the new point is measured on the inside surface of the cavity.

Returning to operation 1002, if additional measurements are not desired in the same plane, then the process determines if additional measurements are desired in a different plane (operation 1010). If additional measurements are desired in a different plane, then the process issues a command to cause the scanning mechanism to move the mounting arm such that the scanning mechanism can measure a parameter in a new plane relative to the cavity (operation 1012). For example, in response to the processor command, a robot attached to the scanning mechanism moves a distance inside the cavity, thereby moving the mounting arm that distance inside the cavity.

The scanning system then measures a new translated position of the mounting arm using the tracking mechanism. As a result, the process receives input data corresponding to the newly translated position of the scanning mechanism (operation 1014). In this illustrative example, the tracking mechanism measures the new position of the scanning mechanism relative to the tracking mechanism or some other frame of reference. The process then returns to operation 1000 to measure a parameter of yet another point on the inside surface of the cavity.

The process continues to repeat between operations 1000 and 1014 as described until no additional measurements in a different plane are desired in operation 1010. Thereafter, the process terminates. The scanning mechanism can then be removed from the cavity and inserted into another cavity of the same object.

Figure 11:
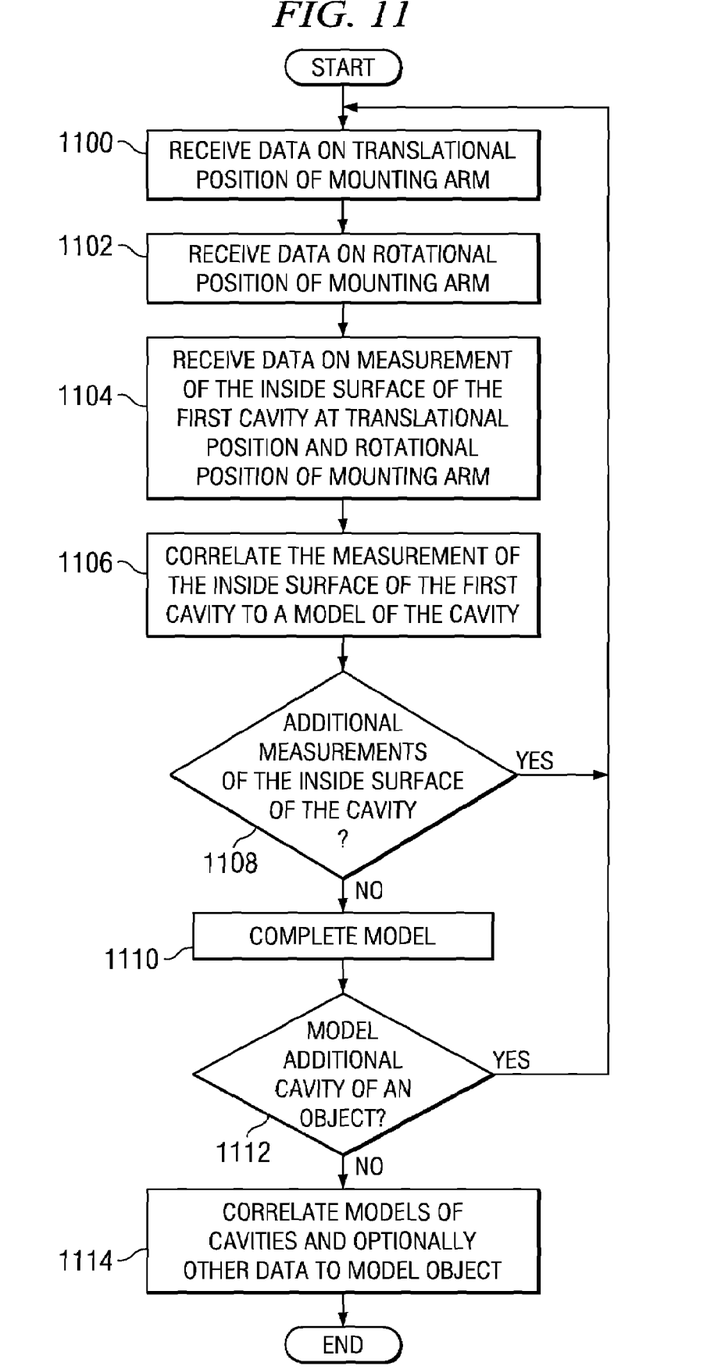
FIG. 11 is a flowchart of a process for modeling a cavity in accordance with an advantageous embodiment of the present invention.

With reference now to FIG. 11, a flowchart of a process for modeling a cavity is depicted in accordance with an advantageous embodiment of the present invention. The process described in FIG. 11 may be implemented using a scanning system, such as scanning system 100 described in FIG. 1. In an exemplary illustrative embodiment, the process described in FIG. 11 is implemented using computer usable program code in a recordable-type medium to model a cavity of a horizontal stabilizer. The computer usable program code executing the process in FIG. 11 may be executed in a processing unit, such as processing unit 900 of FIG. 9.

The process begins by receiving data on a translational position of the mounting arm of the scanning mechanism (operation 1100). The process then receives data on the rotational position of the mounting arm of the scanning mechanism (operation 1102). The process continues by receiving data on a measurement of the inside surface of a first cavity at the translational position and rotational position of the mounting arm (operation 1104). The measurement of the inside surface of the first cavity is correlated to a model of the first cavity (operation 1106).

The process then determines whether additional measurements of the inside surface of the cavity are desired (operation 1108). If additional measurements are desired, then the process returns to operation 1100 and repeats. If additional measurements are not desired, then the model of the first cavity is completed based on data points already acquired (operation 1110).

The process then determines whether to model an additional cavity within an object (operation 1112). If a model of an additional cavity is desired, then the process returns to operation 1100 and the process is repeated for the additional cavity. Returning to operation 1112, if no models of additional cavities are desired, then the process correlates models of modeled cavities, as well as optionally other data, to model the object (operation 1114). The process terminates thereafter.

Figure 12:
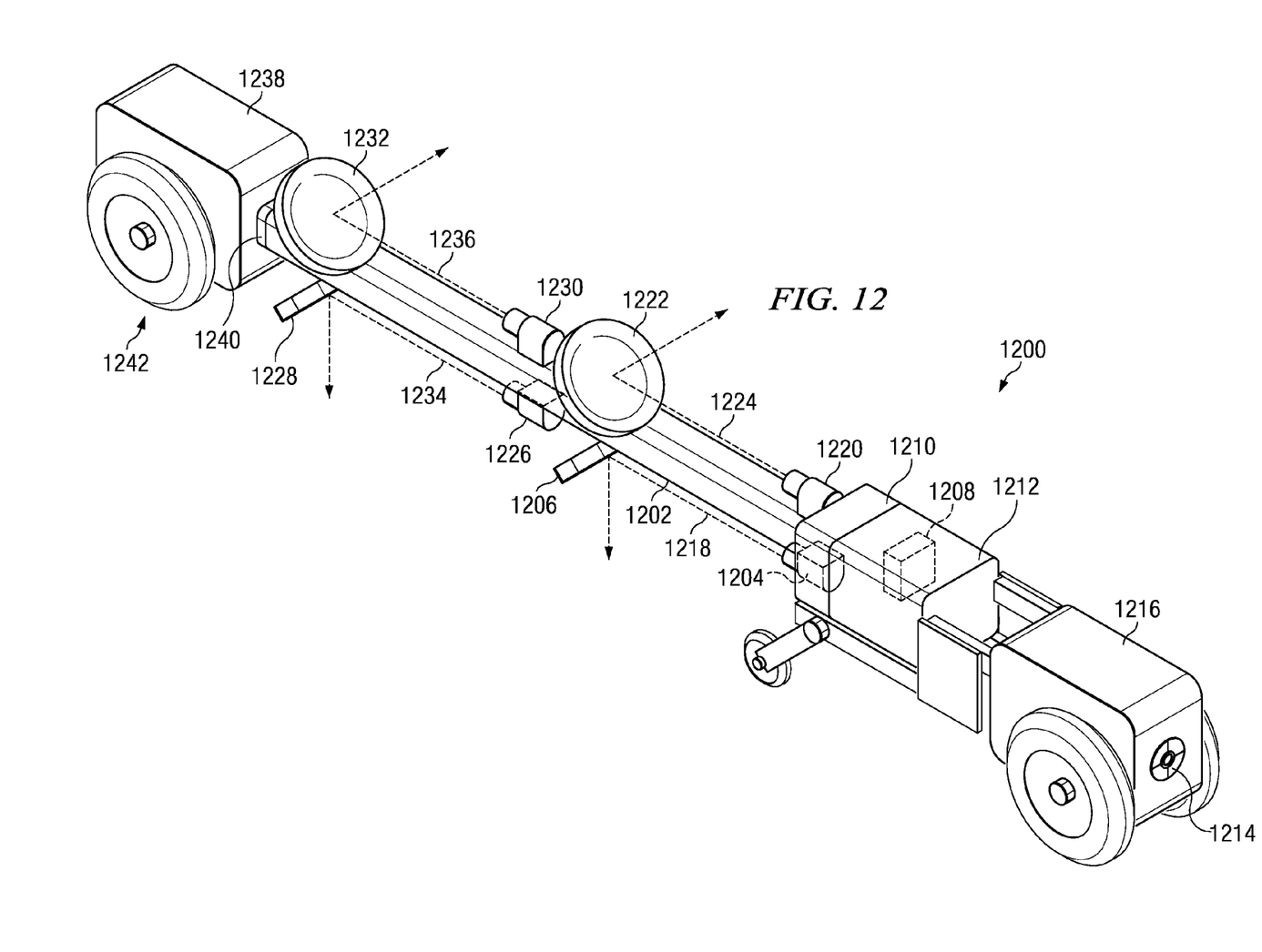
FIG. 12 is a diagram illustrating a perspective view of a scanning mechanism in accordance with an advantageous embodiment of the present invention.

Turning now to FIG. 12, a diagram illustrating a perspective view of a scanning mechanism is depicted in accordance with an advantageous embodiment of the present invention. Scanning mechanism 1200 described in FIG. 12 may be used to implement scanning mechanism 102 of FIG. 1. Scanning mechanism 1200 described in FIG. 12 illustrates an alternative embodiment to scanning mechanism 500 described in FIG. 5.

Scanning mechanism 1200 is similar to scanning mechanism 500 of FIG. 5, in that scanning mechanism 1200 has similar components. For example, scanning mechanism 1200 includes mounting arm 1202, first light source 1204, first mirror 1206, angular encoder 1208, gear reduction assembly 1210, rotating mechanism 1212, retroreflector 1214, and robot 1216. These components are similar to similar components described in FIG. 5 and corresponding components operate similarly to those described in FIG. 5. For example, first light source 1204 may be a measuring system that measures a distance along optical path 1218 to a point on the inside surface of the cavity on which the light falls.

However, scanning mechanism 1200 includes additional components that may be used to increase the rate at which measurements of internal parameters of a cavity are taken. For example, second light source 1220 may be attached to mounting arm 1202 opposite first light source 1204. In a similar manner, second mirror 1222 is attached to mounting arm 1202 opposite first mirror 1206. Second light source 1220 may be a measuring system that measures a distance along optical path 1224 to a point on the inside surface of the cavity on which the light falls. Thus, scanning mechanism 1200 can simultaneously take measurements of internal parameters on multiple points of an inside surface of a cavity.

In addition, if mounting arm 1202 is extended as illustrated in FIG. 12, then still more components may be added to increase the number of measurements scanning mechanism 1200 can take simultaneously. For example, third light source 1226 and corresponding third mirror 1228 may be attached to mounting arm 1202 distally of first mirror 1206 relative to robot 1216. Similarly, fourth light source 1230 and corresponding fourth mirror 1232 may be attached to mounting arm 1202 distally of second mirror 1222 relative to robot 1216. Third light source 1226 may be a measuring system that measures a distance along optical path 1234 to a point on the inside surface of the cavity on which the light falls. Fourth light source 1230 may be a measuring system that measures a distance along optical path 1236 to a point on the inside surface of the cavity on which the light falls. Thus, scanning mechanism 1200 can simultaneously take measurements of parameters on four points of an inside surface of a cavity.

Additional sets of light sources and corresponding mirrors may be attached to mounting arm 1202 at various points on and around mounting arm 1202. Any desired number of light sources and corresponding mirrors may be attached to mounting arm 1202, subject to physical space available on the mounting arm.

Because mounting arm 1202 is long, additional support may be desirable for mounting arm 1202. Thus, scanning mechanism 1200 can include housing 1238. Housing 1238 is a rigid object rotatably attached to mounting arm 1202 via rotational coupling 1240. Rotational coupling 1240 allows rotation of mounting arm 1202 without rotating housing 1238. Second robot 1242 may be added to housing 1238 in order to facilitate moving scanning mechanism 1200 within a cavity. However, second robot 1242 may be replaced with any support, such as posts, passive wheels, or passive or driven treads that support mounting arm 1202 and that allow scanning mechanism 1200 to move within a cavity.

Thus, the advantageous embodiments described herein provide a method and apparatus to measure a set of internal parameters of a cavity within an object. Specifically, a scanning mechanism for scanning an internal parameter of a cavity within an object may include a rotating mechanism and a mounting arm rotatably attached to the rotating mechanism. The scanning mechanism also includes a light source connected to the mounting arm. The light source emits a light. A mirror is connected to the mounting arm, the mirror positioned to reflect the light. The scanning mechanism also includes a measuring system that measures a parameter associated with an object on which the light falls, the measuring system attached to the mounting arm.

The different embodiments of the scanning mechanism described herein provide several advantages over known solutions for measuring various parameters of a cavity within an object. For example, the illustrative embodiments of the scanning mechanism described herein allow parameters of a cavity within an object to be measured without destroying or modifying the object. Additionally, illustrative embodiments of the scanning mechanism described herein allow a three dimensional model of the inside surfaces of cavities within an object to be modeled. No known system or device can perform these functions, particularly in cavities of varying dimensions in large objects, such as horizontal stabilizers or other aircraft parts. Thus, the illustrative embodiments described herein are particularly useful for measuring a set of internal parameters of a horizontal stabilizer or other wing of an aircraft. However, not all embodiments described herein provide the same advantages or the same degree of advantage.

Additionally, measurements of a set of internal parameters can be performed on cavities of various shapes and sizes. For example, the illustrative embodiments described herein may be used to perform measurements of a set of internal parameters of an irregularly shaped cavity. Additionally, the illustrative embodiments described herein may be used to obtain measurements of a circumference of a circular cavity that might vary in dimensions according to some specification for the object. Thus, illustrative embodiments described herein can be used to measure a wide variety of cavities in a wide variety of objects.

The description of the present invention has been presented for purposes of illustration and description, and is not intended to be exhaustive or limited to the invention in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the invention, the practical application, and to enable others of ordinary skill in the art to understand the invention for various embodiments with various modifications as are suited to the particular use contemplated.

What is claimed is:

1. An apparatus comprising:
   a scanning mechanism, wherein the scanning mechanism comprises:
      a rotating mechanism;
      a mounting arm rotatably attached to the rotating mechanism;
      a light source connected to the mounting arm, wherein the light source emits a coherent light;
      a mirror connected to the mounting arm, wherein the mirror is positioned to reflect the coherent light; and
      a measuring system, wherein the measuring system measures a parameter associated with an object on which the coherent light falls, and wherein the measuring system is attached to the mounting arm;
   a tracking mechanism in communication with the scanning mechanism, wherein the tracking mechanism measures a distance from the tracking mechanism to the scanning mechanism; and
   a processing unit in communication with the scanning mechanism and the tracking mechanism, wherein the processing unit collects measurement information from the scanning mechanism and the tracking mechanism.

2. The apparatus of claim 1 further comprising:
   an angular encoder connected to the mounting arm such that the angular encoder can measure a change in a rotational position of the mounting arm.

3. The apparatus of claim 1 further comprising:
   a robot connected to the scanning mechanism, wherein the robot moves the scanning mechanism within a cavity within the object.

4. The apparatus of claim 1 further comprising:
   a second light source connected to the mounting arm, wherein the second light source emits a second coherent light;
   a second mirror connected to the mounting arm, wherein the second mirror is positioned to reflect the second coherent light; and
   a second measuring system, wherein the second measuring system measures the parameter associated with the object on which the coherent light falls and wherein the second measuring system is attached to the mounting arm.

5. The apparatus of claim 1 further comprising:
   a memory in communication with the processing unit, the memory containing instructions executable to form a model of the inside of the object based on measurements made by the measuring system.

6. The apparatus of claim 1 further comprising:
   a gear reduction assembly attached to the rotating mechanism and to the mounting arm.

7. The apparatus of claim 1 further comprising:
a retroreflector attached to the rotating mechanism, wherein the tracking mechanism is an interferometer and wherein the tracking mechanism is in communication with the scanning mechanism via light reflected between the interferometer and the retroreflector.

8. A scanning mechanism comprising:
a rotating mechanism;
a mounting arm rotatably attached to the rotating mechanism;
a light source connected to the mounting arm, wherein the light source emits a coherent light;
a mirror connected to the mounting arm, wherein the mirror is positioned to reflect the coherent light;
a retroreflector attached to the rotating mechanism, wherein the retroflector allows for tracking a relative location of the scanning mechanism; and
a measuring system, wherein the measuring system measures a parameter associated with an object on which the coherent light falls and wherein the measuring system is attached to the mounting arm.

9. The scanning mechanism of claim 8 further comprising:
an angular encoder connected to the mounting arm such that the angular encoder can measure a change in a rotational position of the mounting arm.

10. The scanning mechanism of claim 8 further comprising:
a robot connected to the mounting arm, the wherein robot moves the mounting arm within a cavity within an object.

11. The scanning mechanism of claim 8 further comprising:
a second light source connected to the mounting arm, wherein the second light source emits a second light;
a second mirror connected to the mounting arm, wherein the second mirror is positioned to reflect the second light; and
a second measuring system, wherein the second measuring system measures the parameter associated with the object on which the light falls and wherein the second measuring system is attached to the mounting arm.

12. The scanning mechanism of claim 8 further comprising:
a gear reduction assembly attached to the rotating mechanism and to the mounting arm.

13. The scanning mechanism of claim 8 wherein the measuring system is a triangulation base measuring system.

14. The scanning mechanism of claim 8 wherein the parameter is a distance along an optical path between the measuring system and the object.

15. A method for measuring a parameter inside a cavity within an object, the method comprising:
placing a scanning mechanism into the cavity;
directing a light from a light source onto a portion of an inside surface of the cavity, wherein the light source is connected to a mounting arm of the scanning mechanism and wherein the mounting arm is rotatably connected to a rotating mechanism of the scanning mechanism; and
measuring an internal parameter of the cavity using a measuring system connected to the mounting arm of the scanning mechanism;
tracking a relative location of the scanning mechanism using a tracking mechanism, wherein the tracking mechanism determines a distance between the tracking mechanism and the scanning mechanism; and
collecting measurement information from the scanning mechanism and the tracking mechanism using a processing unit that is in communication with the scanning mechanism and the tracking mechanism.

16. The method of claim 15 wherein the parameter is a distance and wherein the measuring step comprises:
measuring a distance along an optical path between the measuring system and the portion to form a first measurement.

17. The method of claim 16 further comprising:
rotating the mounting arm through an angle and repeating the measuring step to form a second measurement.

18. The method of claim 15 further comprising:
measuring a position of the scanning mechanism relative to a reference.

19. The method of claim 17 further comprising:
measuring a position of the scanning mechanism relative to a reference to form a third measurement.

20. The method of claim 19 further comprising:
modeling the cavity using the first measurement, the second measurement, and the third measurement.

21. A scanning mechanism comprising:
a rotating mechanism;
a mounting arm rotatably attached to the rotating mechanism;
a first light source connected to the mounting arm, wherein the first light source emits a first coherent light;
a first mirror connected to the mounting arm, wherein the first mirror is positioned to reflect the first coherent light;
a first measuring system, wherein the first measuring system measures a first parameter associated with an object on which the first coherent light falls and wherein the first measuring system is attached to the mounting arm;
a second light source connected to the mounting arm, wherein the second light source emits a second coherent light;
a second mirror connected to the mounting arm, wherein the second mirror is positioned to reflect the second coherent light; and
a second measuring system, wherein the second measuring system measures a second parameter associated with the object on which the second coherent light falls and wherein the second measuring system is attached to the mounting arm.

* * * * *